United States Patent
Iino et al.

(10) Patent No.: US 8,059,279 B2
(45) Date of Patent: Nov. 15, 2011

(54) METHOD AND SYSTEM FOR INSPECTING TIRE SURFACE

(75) Inventors: Hirotaka Iino, Kodaira (JP); Tomoyuki Kaneko, Kodaira (JP); Takao Kokubu, Kodaira (JP)

(73) Assignee: Bridgestone Corporation, Tokyo (JP)

( * ) Notice: Subject to any disclaimer, the term of this patent is extended or adjusted under 35 U.S.C. 154(b) by 81 days.

(21) Appl. No.: 12/447,759

(22) PCT Filed: Oct. 23, 2007

(86) PCT No.: PCT/JP2007/070596
§ 371 (c)(1),
(2), (4) Date: Jun. 26, 2009

(87) PCT Pub. No.: WO2008/053742
PCT Pub. Date: May 8, 2008

(65) Prior Publication Data
US 2010/0002244 A1    Jan. 7, 2010

(30) Foreign Application Priority Data
Nov. 2, 2006    (JP) .................................. 2006-298485

(51) Int. Cl.
*G01B 11/24*    (2006.01)
(52) U.S. Cl. ....... 356/601; 382/141; 73/146; 356/237.1; 356/237.5
(58) Field of Classification Search .................. 356/601, 356/237.1–237.6; 382/141; 73/146
See application file for complete search history.

(56) References Cited

U.S. PATENT DOCUMENTS
6,064,477 A * 5/2000 Matsumoto et al. ....... 356/237.2
6,124,925 A * 9/2000 Kaneko et al. ............. 356/237.1
(Continued)

FOREIGN PATENT DOCUMENTS
EP    1 477 765 A1    11/2004
(Continued)

OTHER PUBLICATIONS
Supplementary European Search Report dated Nov. 24, 2009 (7 pages).

*Primary Examiner* — Tarifur Chowdhury
*Assistant Examiner* — Isiaka Akanbi
(74) *Attorney, Agent, or Firm* — Sughrue Mion, PLLC (57) ABSTRACT

Disclosed is a tire surface inspecting technique capable of surely discriminating rubber pieces of a quality different from that of a tire embedded in the surface of the tire by vulcanization from the tire. A first illuminating unit 11 include paired first light projectors 11a and 11b that project light respectively from opposite sides toward an objective line L on a tire T. A second illuminating unit 12 include paired second light projectors 12a and 12b that project light respectively from opposite sides toward the objective line L in a direction different from that in which the first illuminating unit 11 project light. The first illuminating unit 11 and the second illuminating unit 12 operate alternately for illumination. The line camera 3 forms an image of a part of the surface of the tire corresponding to the objective line L in synchronism with the respective illuminating operations of the first and second illuminating unit. Illumination and image formation are repeated for different parts of the surface of the tire that are moved successively to a position corresponding to the objective line L. Images formed by the line camera are analyzed for the inspection of the surface of the tire T.

6 Claims, 5 Drawing Sheets

U.S. PATENT DOCUMENTS

| | | |
|---|---|---|
| 6,600,567 B2 * | 7/2003 | Kaneko et al. ................. 356/601 |
| 2001/0024279 A1 | 9/2001 | Kaneko et al. |
| 2005/0058333 A1 * | 3/2005 | Kaneko et al. ................. 382/141 |
| 2007/0209431 A1 * | 9/2007 | Fujisawa et al. ................. 73/146 |
| 2008/0273211 A1 * | 11/2008 | Schmitt et al. ................. 356/611 |

FOREIGN PATENT DOCUMENTS

| | | |
|---|---|---|
| JP | 61-180128 A | 8/1986 |
| JP | 10-221267 A | 8/1988 |
| JP | 04-364404 A | 12/1992 |
| JP | 09-096610 A | 4/1997 |
| JP | 11-337502 A | 12/1999 |
| JP | 2001-249012 A | 9/2001 |
| JP | 2003-240521 A | 8/2003 |

* cited by examiner

METHOD AND SYSTEM FOR INSPECTING TIRE SURFACE

CROSS REFERENCE TO RELATED APPLICATIONS

This application is a National Stage of International Application No. PCT/JP2007/070596 filed Oct. 23, 2007, claiming priority based on Japanese Patent Application No. 2006-298485 filed Nov. 2, 2006, the contents of all of which are incorporated herein by reference in their entirety.

TECHNICAL FIELD

The present invention relates to a method of inspecting a tire surface and a system for inspecting a tire surface.

BACKGROUND ART

Tires are inspected for roundness, surface unevenness, discoloration, dirty marks, flaws and the like to determine whether the tires are acceptable or not. A known tire surface inspection system is disclosed in Patent document 1.

Patent Document 1: JP 2001-249012 A

The tire surface inspection system disclosed in Patent Document 1 is provided with a linear light-projector having a plurality of LEDs arranged in a line, a line camera capable of forming images of imaging lines illuminated by light projected by the linear light-projector, an area light projector which is a laser light projector, and an area camera capable of forming images of imaging lines illuminated by light projected by the area light projector. The line camera provides appearance data for finding discolored parts and dirty marks. The area camera provides shape data indicating roundness, surface unevenness or flaws.

DISCLOSURE OF THE INVENTION

Problem to be solved by the Invention

The linear light projector projects light always in a fixed illuminating direction on an imaging line on a tire. The line camera receives light reflected by the imaging line to form an image. The line camera receives different quantities of light from parts of the surface of the tire differing from each other in luster and color shade. Therefore, in some cases, parts of the surface of the tire differing from each other in luster and color shade cannot be discriminated by reflecting condition when light is projected in some illuminating directions.

In some cases, rubber fragments remain on the molding surface of a mold after a tire has been vulcanized for shaping in the mold. In such a case, rubber fragments of a material different from that of the tire are embedded in the surface of the vulcanized tire. The rubber fragments thus included in the surface of the tire have surfaces smoothly merging into the surface of the tire and do not form uneven parts. Therefore, the rubber fragments cannot be discriminated from the tire by the difference of the rubber fragments from the tire in luster and color shade.

Therefore, when rubber fragments are integrally embedded in the surface of the tire by vulcanization, the known inspection system that projects light on the surface of the tire in a fixed illuminating direction and forms images of the illuminated parts of the tire can not always surely discriminate the rubber fragments from the tire because color and monochromatic images formed by the line camera by processing the reflected light cannot represent delicate luster and color shades of the rubber fragments when illuminating light is projected on the tire in some illuminating directions.

The present invention has been made in view of those problems and it is therefore an object of the present invention to provide a tire surface inspecting method capable of surely distinguishing rubber pieces of a different quality embedded in the surface of a tire by vulcanization and a tire surface inspection system for carrying out the tire surface inspecting method.

Means for Solving the Problem

To attain the above object, the present invention provides a tire surface inspecting method comprising the steps of: placing a line camera at a predetermined position with respect to a surface of a tire to be inspected; setting an objective line on a part of the surface of the tire; projecting light toward the objective line; forming an image of a part of the surface of the tire corresponding to the objective line by the line camera; and analyzing images formed by the line camera to inspect the surface of the tire;

wherein tire surface inspecting method further comprises the steps of:

providing a first illuminating means including paired first light projectors for projecting light toward the objective line from opposite sides, respectively, with respect to the objective line, and a second illuminating means including paired second light projectors for projecting light toward the objective line respectively from opposite sides in an illuminating direction different from that in which the first illuminating means illuminates;

alternately operating the first and second illuminating means to alternately illuminate a part of the surface of the tire corresponding to the objective line;

operating the line camera to form an image of the part of the surface of the tire corresponding to the objective line for analysis in synchronism with the illuminating operations of the first and second illuminating means; and repeating the step of alternately operating the first and second illuminating means and the step of operating the line camera with the objective line on the surface of the tire changed in position.

In a preferred embodiment of the invention, the paired first light projectors include first linear light projectors extending parallel to the objective line on the surface of the tire, and the paired second light projectors include second linear light projectors extending perpendicularly to the objective line.

The paired first light projectors and the paired second light projectors may be arranged in a quadrilateral as viewed in a direction toward the surface of the tire.

The paired first light projectors and the paired second light projectors may be arranged on four sides, respectively, of a quadrilateral having a diagonal parallel to the objective line as viewed in a direction toward the surface of the tire.

To attain the above object, the present invention also provides a tire surface inspection system comprising: a support means for supporting a tire thereon with one side surface of the tire facing upward; an illuminating means for illuminating an objective line set on the surface of the tire supported on the support means; and a line camera placed at a fixed position to form an image of a part corresponding to the objective line and illuminated by the illuminating means; wherein the illuminating means includes: a first illuminating means including paired first light projectors that project light toward the objective line in illuminating directions from the opposite sides, respectively, with respect to the objective line; and a second illuminating means including paired second light projectors that project light respectively from opposite sides toward the objective line in illuminating directions different from the illuminating directions in which the first illuminating means illuminates the objective line, respectively; and the tire surface inspection system further comprises:

a turning means for turning the support means to turn the tire; and a control means for controlling the line camera and the turning means, wherein the control means carries out control operations for driving the turning means for turning such that the objective line is moved successively to different parts of the surface of the tire and for driving the line camera in synchronism with the illuminating operations of the first and second illuminating means such that images of parts of the surface of the tire successively brought into coincidence with the objective line are formed sequentially.

EFFECT OF THE INVENTION

The tire surface inspecting method of the present invention forms an image of a part of the surface of the tire corresponding to the objective line by the line camera in synchronism with the alternate illuminating operations of the first and the second illuminating means that illuminate the tire respectively in different directions. Therefore, rubber pieces of a quality different from that of the tire, embedded in the surface of the tire by vulcanization can be surely discriminated from the tire through analysis of the images of the parts of the surface of the tire illuminated at least by either of the first and second illuminating means and formed by the line camera.

Each of the first and the second illuminating means includes the paired illuminating means that project light toward the objective line respectively from opposite sides with respect to the objective line. Therefore, light can be concentrated on the part of the surface of the tire corresponding to the objective line, the line camera can receive a large quantity of reflected light to form an image, the line camera can form an image providing color information and having a high contrast tone. Such an image facilitates discriminating the rubber pieces of a different quality embedded in the tire by vulcanization from the tire.

The tire surface inspecting method in an embodiment illuminates the part of the surface of the tire corresponding to the objective line efficiently by the paired first linear light projectors extending parallel to the objective line on the surface of the tire, and the paired second linear light projectors extending perpendicularly to the objective line. Therefore, the line camera can form a clear image.

The control means of the tire surface inspection system of the present invention drives the turning means to turn the tire such that parts of the surface of the tire is moved successively to a position corresponding to the objective line, drives the line camera in synchronism with the illuminating operations of the first and second illuminating means that illuminate the tire respectively in different directions to form images of the parts of the surface of the tire moved to the position corresponding to the objective line successively. Therefore, rubber pieces of a quality different from that of the tire, embedded in the surface of the tire by vulcanization can be surely discriminated from the tire through analysis of images of parts of the surface of the tire illuminated at least by either of the first and second illuminating means and formed by the line camera.

REFERENCE CHARACTERS

T . . . Tire, L . . . Objective line 1 . . . Tire surface inspection system, 2 . . . Turning table, 3 . . . Line camera, 11 . . . First illuminating unit, 11$a$ and 11$b$ . . . First linear light projectors, 12 . . . Second illuminating unit, 12$a$ and 12$b$ . . . Second linear light projectors, 15 . . . Turning table drive motor, 16 . . . Display, 21 . . . Illumination control unit, 22 . . . Camera control unit, 23 . . . Motor control unit, 24 . . . Image processing unit, 31 . . . External image forming device, 32 . . . External condition evaluating device, 33 . . . Image forming device, 51 . . . Tire surface inspection system, 52 . . . Turning table, 53 . . . Line camera, 61 . . . First illuminating unit, 61$a$ and 61$b$ . . . First linear light projectors, 62 . . . Second illuminating unit, 62$a$ and 62$b$ . . . Second linear light projector

BEST MODE FOR CARRYING OUT THE INVENTION

A preferred embodiment of the present invention will be described with reference to FIGS. 1 to 4.

Figure 1:
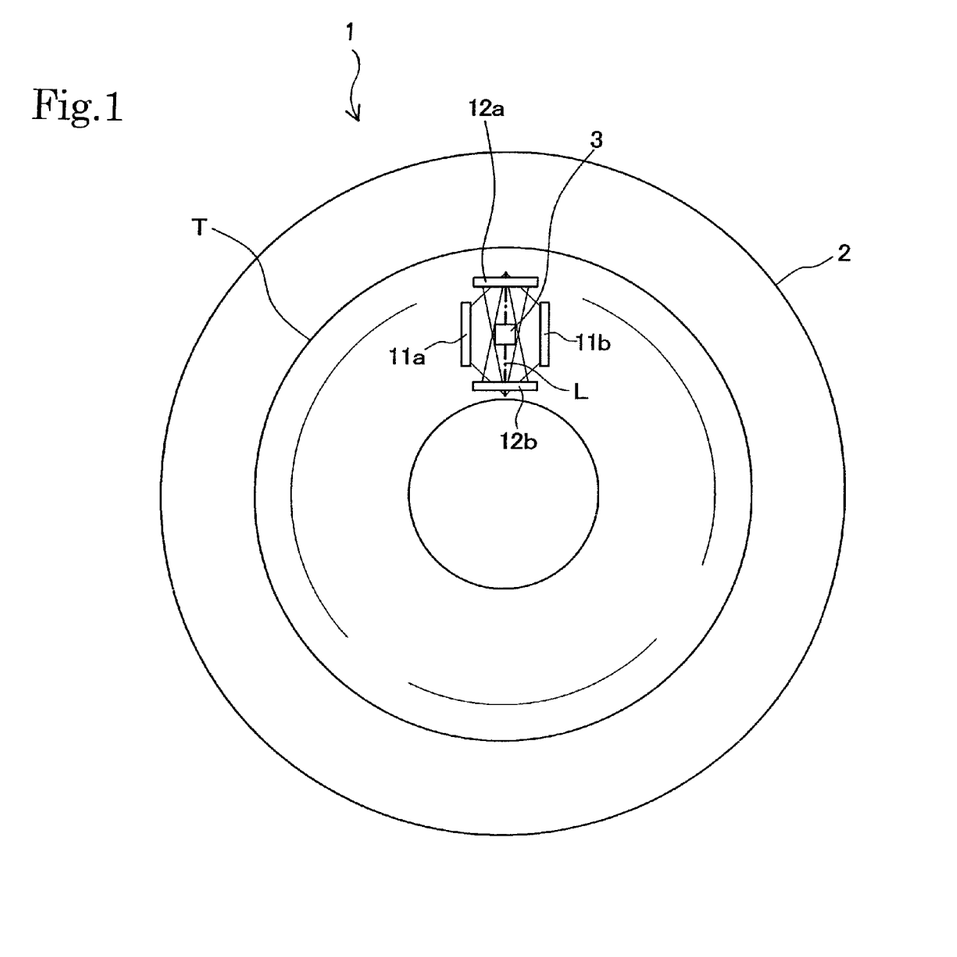
FIG. 1 is a top plan view of a tire surface inspection system in a first embodiment of the present invention.

Referring to FIG. 1, a tire surface inspection system 1 in a first embodiment of the present invention has a horizontal turning table 2. A vulcanized tire T is mounted on the turning table 2 with its center axis aligned with the center axis of the turning table 2. The tire T mounted on the turning table 2 is subjected to a visual inspection. The turning table 2 is a support means for supporting a tire thereon.

A line camera 3 is fixedly set at a predetermined position above a side surface facing up of the tire T mounted on the turning table 2 such that the line camera 3 faces the side surface.

The line camera 3 is a CCD camera having pixels arranged in a line. The line camera 3 is provided with an optical wavelength filter that passes monochromatic slit light of a specific wavelength selectively. The line camera 3 can form an image of the monochromatic slit light that has passed the optical wavelength filter.

Figure 2:
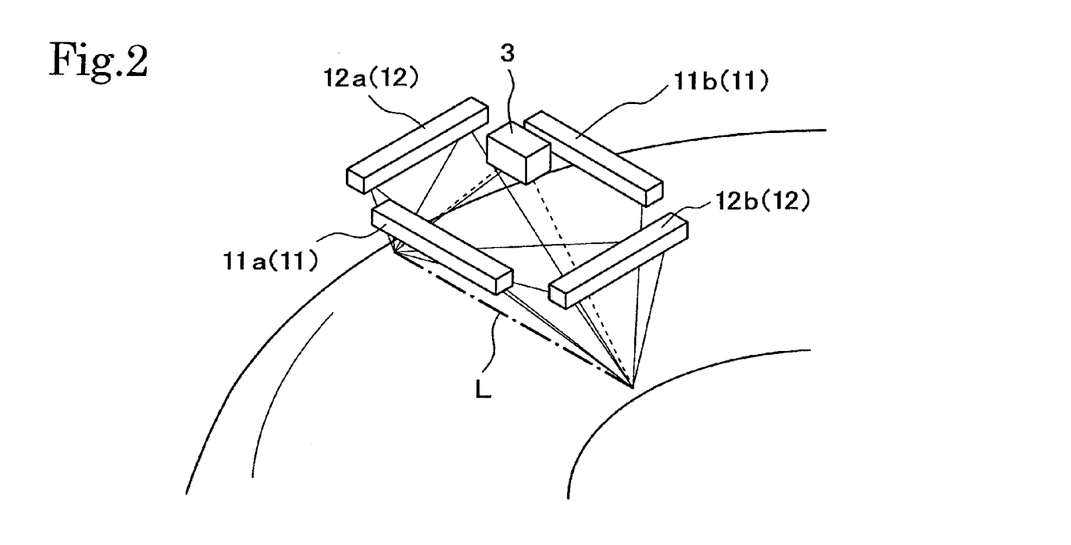
FIG. 2 is a perspective view of an essential part of the tire surface inspection system shown in FIG. 1.

Referring to FIG. 2, the line camera 3 sets an objective line L on the surface of the tire T. The objective line L extends on and along a radius of the tire T. The objective line L is indicated by a chain line in FIGS. 1 and 2. The line camera 3 forms an image of a part of the surface of the tire T corresponding to the objective line L. Although the objective line L is straight in a top plan view, the objective line L is actually curved along the side surface of the tire T as viewed from a circumferential direction.

A first illuminating unit 11 includes paired first linear light projectors 11$a$ and 11$b$. Each of the first linear light projectors 11$a$ and 11$b$ is provided with a plurality of light sources arranged in a line. The first linear light projectors 11$a$ and 11$b$ are disposed obliquely above the objective line L set on the surface of the tire T so as to extend parallel to the objective line L. The first linear light projectors 11$a$ and 11$b$ project light obliquely on the objective line L from the opposite sides, respectively, with respect to the objective line L.

A second illuminating unit 12 includes paired second linear light projectors 12$a$ and 12$b$. The second linear light projectors 12a and 12b are disposed above the opposite ends, respectively, of the objective line L so as to extend perpendicularly to the objective line L. The paired second linear light projectors 12a and 12b of the second illuminating unit 12 project light toward the objective line L respectively from opposite sides with respect to a direction in which the objective line L extends.

As obvious from FIG. 1, the paired first linear light projectors 11a and 11b and the paired second linear light projectors 12a and 12b are extended on the four sides, respectively, of a rectangle as viewed from above the side surface of the tire T.

The line camera 3 forms an image of a part of the surface of the tire T corresponding to the objective line L illuminated by light emitted from the first illuminating unit 11 or the second illuminating unit 12.

The first illuminating unit 11 and the second illuminating unit 12 emit light alternately at predetermined points of time. The line camera 3 is controlled so as to form images of a part corresponding to the objective line L at the predetermined points of time.

Figure 3:
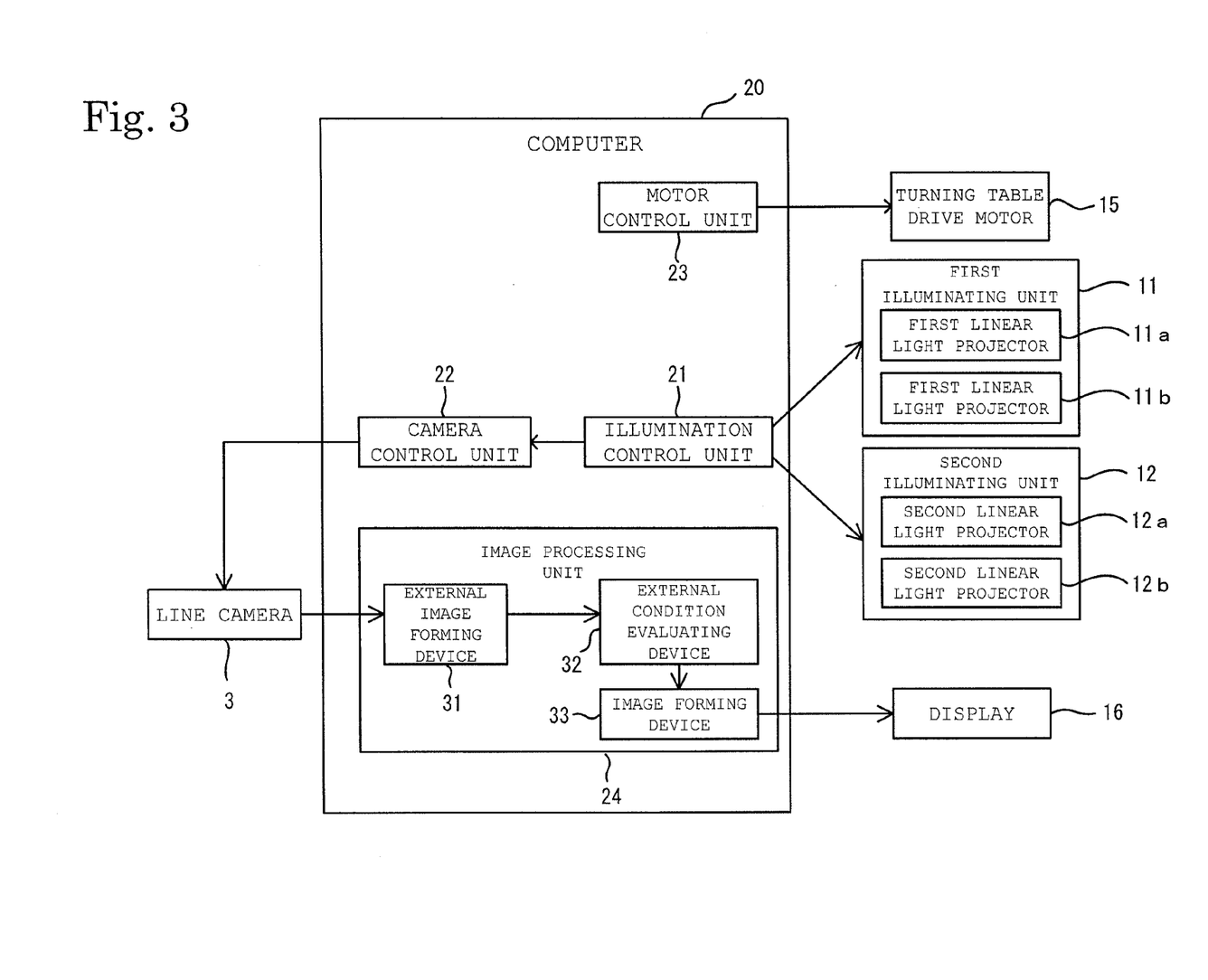
FIG. 3 is a general block diagram of a controller included in the tire surface inspection system shown in FIG. 1.

A computer 20, namely, an inspection system controller, controls the tire-inspection system 1. FIG. 3 shows the computer 20, namely, the controller, in a schematic block diagram.

The computer 20 includes an illumination control unit 21, a camera control unit 22, a motor control unit 23 and an image processing unit 24.

The illumination control unit 21 actuates the first illuminating unit 11 and the second illuminating unit 12 alternately at the predetermined points of time to illuminate the part corresponding to the objective line L. The camera control unit 22 actuates the line camera 3 in synchronism with the respective illuminating operations of the first illuminating unit 11 and the second illuminating unit 12 to form images of the illuminated part of the surface of the tire T corresponding to the objective line L.

The motor control unit 23 controls the operation of the turning table drive motor 15 for driving the turning table 2.

The image processing unit 24 includes an external image forming device 31, an external condition evaluating device 32 and an image forming device 33. The external image forming device 31 constructs an external image, using appearance date received from the line camera 3. The external condition evaluating device 32 evaluates the external image to decide whether or not the appearance is acceptable. The image forming device 33 gives results of evaluation to a display 16 and the display 16 displays the results of evaluation.

Figure 4:
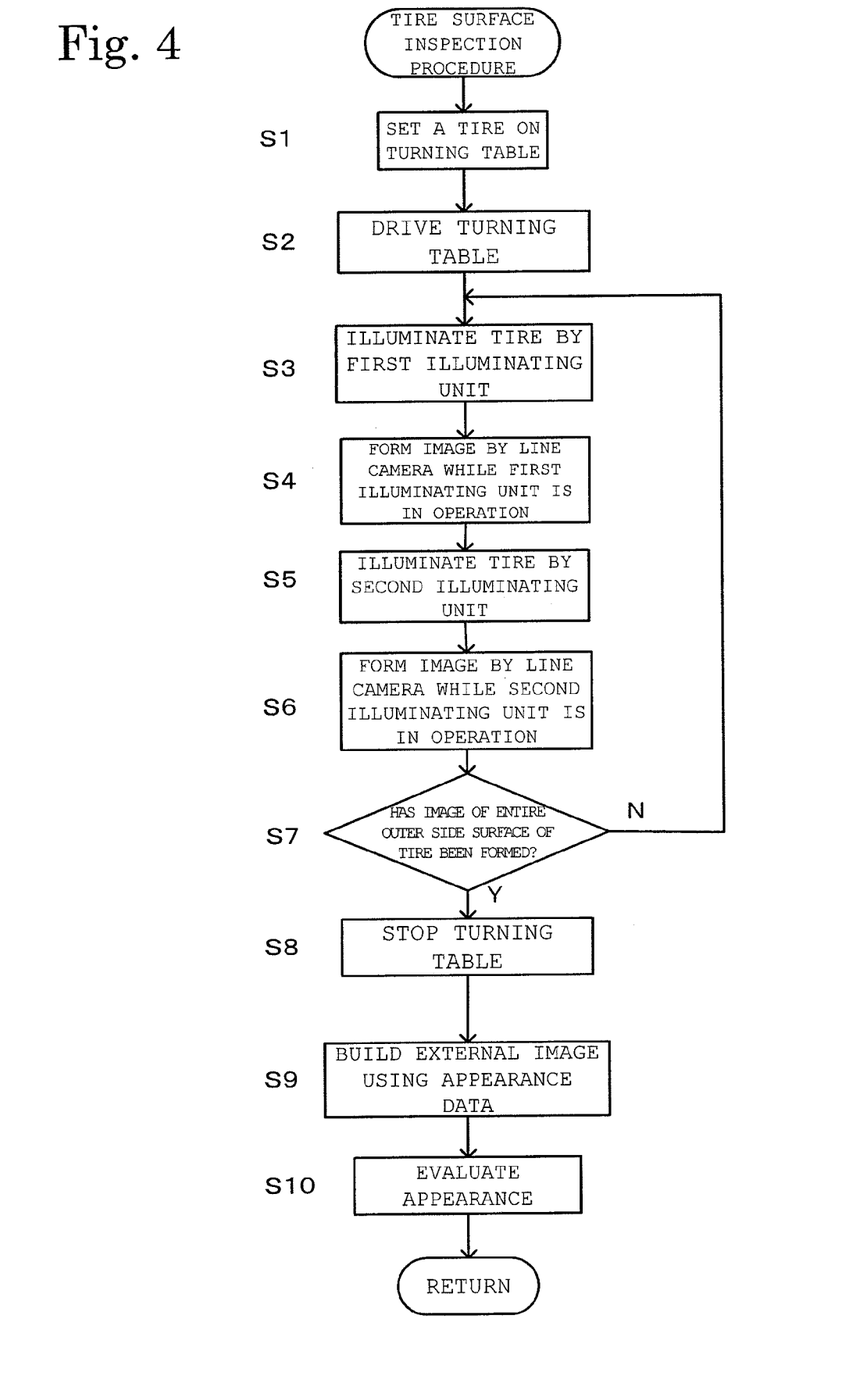
FIG. 4 is a flow chart of a control procedure to be carried out by the tire surface inspection system shown in FIG. 1.

A control procedure to be carried out by the tire surface inspection system 1 will be described with reference to a flow chart shown in FIG. 4.

First, the tire T is placed at a predetermined position on the turning table 2 (step S1). The motor control unit 23 drives the turning table drive motor 15 to turn the turning table 2 holding the tire T thereon at a predetermined rotational speed of, for example, one turn per 10 second (step S2).

In step S3, the first illuminating unit 11 is driven to project light toward the objective line L on the surface of the tire T by the first linear light projectors 11a and 11b.

At the same time the line camera 3 forms an image of the part of the surface of the tire T corresponding to the imaging line L and illuminated by the first linear light projectors 11a and 11b (step S4).

Subsequently, the second illuminating unit 12 is driven in step S5 to project light toward the objective line L on the surface of the tire T by the second linear light projectors 12a and 12b in a direction at an angle of 90° to the direction in which the first linear light projectors 11a and 11b project light.

At the same time the line camera 3 forms an image of the part of the surface of the tire T corresponding to the imaging line L and illuminated by the second linear light projectors 12a and 12b (step S6).

In step S7, a query is made to see if an image of the entire outer side surface of the tire T has been formed. If the response to the query in step S7 is negative, steps S3, S4, S5 and S6 are repeated to successively form images of parts that correspond successively to the objective line L as the tire T is turned and illuminated alternately by the first illuminating unit 11 and the second illuminating unit 12 at predetermined points of time.

After an image of the entire side surface has been formed, the procedure goes from step S7 to step S8 to stop the turning table 2.

In step S9, the external image forming device 31 builds an external image, using the appearance data provided by the line camera 3. Then, in step S10, the external condition evaluating device 32 decides whether or not the appearance is acceptable. It is decided that the appearance is acceptable when densities of parts of the external image are within an allowable density range or unacceptable when densities of parts of the external image are not within the allowable density range. The image forming device 33 gives results of evaluation to the display 16 and the display 16 displays the results of evaluation.

When rubber fragments are embedded in the surface of the tire by vulcanization, color and monochromatic images formed by the line camera by processing the reflected light can not always represent the delicate luster and color shades of the rubber fragments when illuminating light is projected on the tire from some illuminating directions when the tire is inspected by the known inspecting method.

When the external appearance of the tire is inspected by this tire surface inspection system 1, the line camera 3 forms an image of a part of the surface of the tire corresponding to the objective line in synchronism with illumination from different directions by the alternate operations of the first illuminating unit 11 and the second illuminating unit 12. Therefore, rubber pieces of a quality which is different from that of the tire T embedded in the surface of the tire T by vulcanization and which is difficult to discriminate from the tire T can be clearly represented by color and densities in the images formed by the line camera 3 when the tire T is illuminated by at least either of the first illuminating unit 11 and the second illuminating unit 12. Thus, the rubber pieces of a quality different from that of the tire T embedded in the surface of the tire T can be surely discriminated from the tire T.

An image of a part of the surface of the tire T corresponding to the objective line is formed by alternately operating the first illuminating unit 11 and the second illuminating unit 12 while the tire T is being turned. Therefore, images of different parts of the surface of the tire T are formed successively. Since an image is formed in a short time and the external image forming device 31 constructs a continuous image, the same effect as the formation of an image of substantially the same positions by changing the illuminating direction can be expected and hence the rubber pieces of the different quality embedded in the surface of the tire T can be easily discriminated from the tire T.

The first illuminating unit 11 includes the paired linear light projectors that project light on the part of the surface of the tire T corresponding to the objective line L respectively from the opposite sides with respect to the objective line L, and the second illuminating unit 12 includes the paired linear light projectors that project light on the part of the surface of the tire T corresponding to the objective line respectively from the opposite sides respectively corresponding to the opposite ends of the objective line L. Therefore, light can be concentrated on the part of the surface of the tire T corresponding to the objective line L, the line camera 3 can receive a large quantity of reflected light to form an image, the line camera can form an image having clear colors and a high contrast tone. Such an image facilitates discriminating the rubber pieces of a different quality embedded in the surface of the tire T by vulcanization still further.

Figure 5:
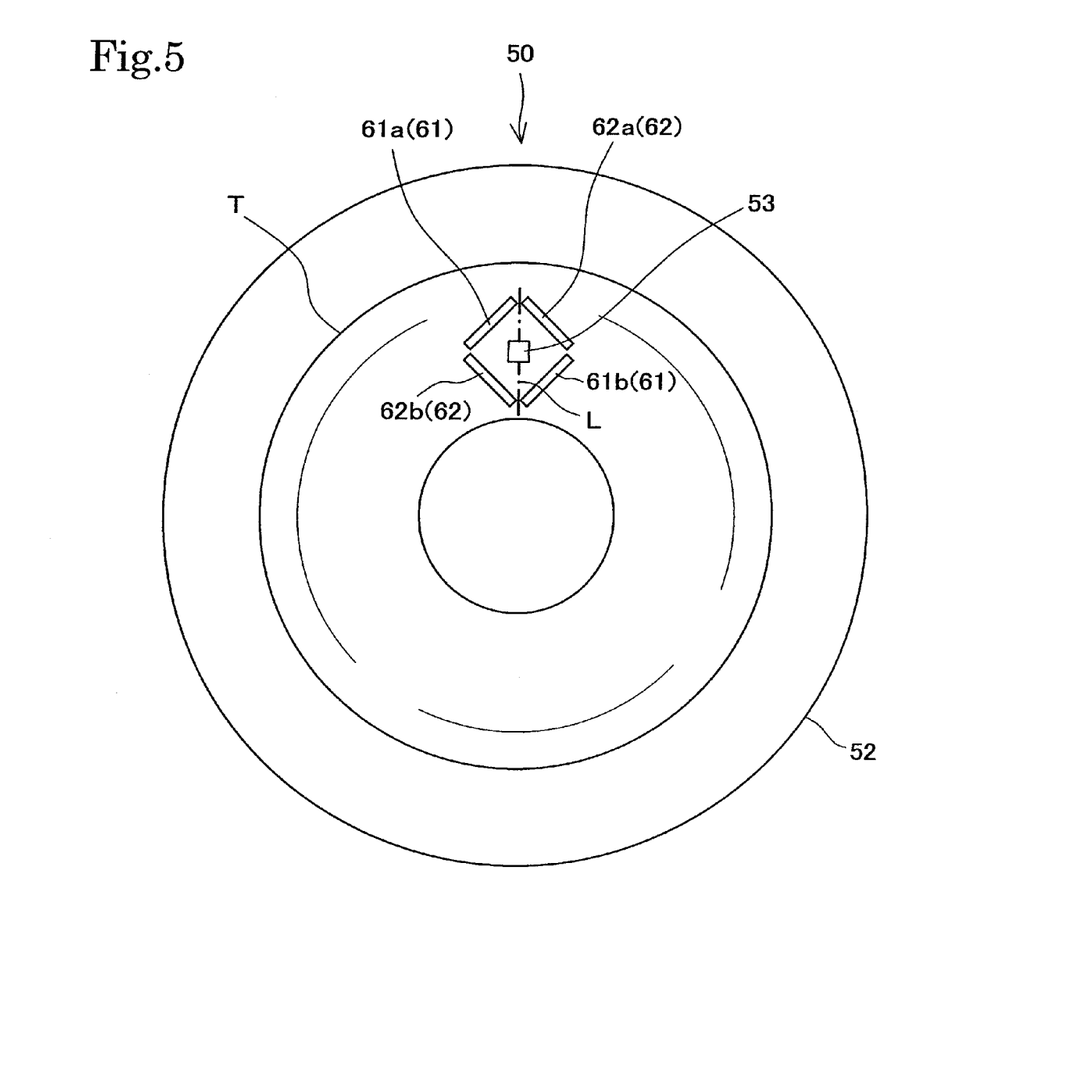
FIG. 5 is a top plan view of a tire surface inspection system in a second embodiment of the present invention.

A tire surface inspection system 50 in a second embodiment of the present invention will be described with reference to FIG. 5.

The tire surface inspection system 50 includes a line camera 53 fixedly set at a predetermined position above a side surface facing up of a tire T mounted on a turning table 52. An objective line L is set on the surface of the tire T. The objective line L extends on a radius of the tire T.

Linear light projectors 61a, 61b, 62a and 62b are disposed obliquely above the objective line L set on the surface of the tire T and are arranged on the sides of a substantially square quadrilateral having a diagonal parallel to the objective line L.

The opposite paired linear light projectors 61a and 61b constitute a first illuminating unit 61, while the paired linear light projectors 62a and 62b constitute a second illuminating unit 62.

The first illuminating unit 61 and the second illuminating unit 62 project light alternately toward the objective line L set on the surface of the tire T respectively in different directions. The line camera 52 is controlled such that timing of image formation by the line camera 52 is synchronous with timing of illumination.

Rubber pieces of a quality which is different from that of the tire T embedded in the surface of the tire T by vulcanization and which is difficult to discriminate from the tire T can be clearly represented by color and densities in the images formed by the line camera 53 when the tire T is illuminated by at least either of the first illuminating unit 61 and the second illuminating unit 62. Thus, the rubber pieces of a quality different from that of the tire T embedded in the surface of the tire T by vulcanization can be surely discriminated from the tire T.

The invention claimed is:

1. A tire surface inspecting method comprising the steps of:
    placing a line camera at a predetermined position with respect to a surface of a tire to be inspected;
    setting an objective line on a part of the surface of the tire;
    projecting light toward the objective line;
    forming an image of a part of the surface of the tire corresponding to the objective line by the line camera; and
    analyzing images formed by the line camera to inspect the surface of the tire;
    wherein tire surface inspecting method further comprises the steps of:
    providing a first illuminating means including paired first light projectors for projecting light toward the objective line from opposite sides, respectively, with respect to the objective line, and a second illuminating means including paired second light projectors for projecting light toward the objective line respectively from opposite sides in an illuminating direction different from that in which the first illuminating means illuminates;
    alternately operating the first and second illuminating means to alternately illuminate a part of the surface of the tire corresponding to the objective line;
    operating the line camera to form an image of the part of the surface of the tire corresponding to the objective line for analysis in synchronism with the illuminating operations of the first and second illuminating means;
    repeating the step of alternately operating the first and second illuminating means and the step of operating the line camera with the objective line on the surface of the tire changed in position;
    using first linear light projectors extending parallel to the objective line set on the surface of the tire, as the paired first light projectors; and
    using second linear light projectors extending perpendicular to the objective line set on the surface of the tire, as the paired second light projectors,
    wherein the paired first light projectors and the paired second light projectors are arranged in a quadrilateral as viewed in a direction toward the surface of the tire.

2. The tire surface inspecting method according to claim 1, wherein the line camera is operated to form the image on the part of the surface of the tire in synchronism with the alternate illuminating operations of the first and second illuminating means.

3. A tire surface inspecting method comprising the steps of:
    placing a line camera at a predetermined position with respect to a surface of a tire to be inspected;
    setting an objective line on a part of the surface of the tire;
    projecting light toward the objective line;
    forming an image of a part of the surface of the tire corresponding to the objective line by the line camera; and
    analyzing images formed by the line camera to inspect the surface of the tire;
    wherein tire surface inspecting method further comprises the steps of:
    providing a first illuminating means including paired first light projectors for projecting light toward the objective line from opposite sides, respectively, with respect to the objective line, and a second illuminating means including paired second light projectors for projecting light toward the objective line respectively from opposite sides in an illuminating direction different from that in which the first illuminating means illuminates;
    alternately operating the first and second illuminating means to alternately illuminate a part of the surface of the tire corresponding to the objective line;
    operating the line camera to form an image of the part of the surface of the tire corresponding to the objective line for analysis in synchronism with the illuminating operations of the first and second illuminating means;
    repeating the step of alternately operating the first and second illuminating means and the step of operating the line camera with the objective line on the surface of the tire changed in position;
    using first linear light projectors extending parallel to the objective line set on the surface of the tire, as the paired first light projectors; and
    using second linear light projectors extending perpendicular to the objective line set on the surface of the tire, as the paired second light projectors,
    wherein the paired first light projectors and the paired second light projectors are arranged on the four sides, respectively, of a quadrilateral having a diagonal parallel to the objective line as viewed in a direction toward the surface of the tire.

4. A tire surface inspection system comprising:
    a support means for supporting a tire thereon with one side surface of the tire facing upward;

an illuminating means for illuminating an objective line set on the surface of the tire supported on the support means; and a line camera placed at a fixed position to form an image of a part corresponding to the objective line and illuminated by the illuminating means;

wherein the illuminating means includes:

a first illuminating means including paired first light projectors that project light toward the objective line in illuminating directions from the opposite sides, respectively, with respect to the objective line; and a second illuminating means including paired second light projectors that project light respectively from opposite sides toward the objective line in illuminating directions different from the illuminating directions in which the first illuminating means illuminates the objective line, respectively;

the tire surface inspection system further comprises:

a turning means for turning the support means to turn the tire; and a control means for controlling the line camera and the turning means;

wherein the control means carries out control operations for driving the turning means for turning such that the objective line is moved successively to different parts of the surface of the tire and for driving the line camera in synchronism with the illuminating operations of the first and second illuminating means such that images of parts of the surface of the tire successively brought into coincidence with the objective line are formed sequentially, wherein the paired first light projectors include first linear light projectors extending in a direction parallel to the objective line set on the surface of the tire, wherein the paired second light projectors include second linear projectors extending in a direction perpendicular to the objective line, and wherein the paired first light projectors and the paired second light projectors are arranged in a quadrilateral as viewed in a direction toward the surface of the tire.

5. The tire surface inspection system according to claim 4, further comprising a turning means for turning the support means to turn the tire, and a control means for controlling the line camera and for controlling the turning means such that the objective line is moved successively to different parts of the surface of the tire, wherein the control means is configured to alternatively operate the first and second illuminating means to alternatively illuminate a part of the surface of the tire corresponding to the objective line and configured to drive the line camera in synchronism with the alternate illuminating operations of the first and second illuminating means.

6. A tire surface inspection system comprising:

a support means for supporting a tire thereon with one side surface of the tire facing upward;

an illuminating means for illuminating an objective line set on the surface of the tire supported on the support means; and a line camera placed at a fixed position to form an image of a part corresponding to the objective line and illuminated by the illuminating means;

wherein the illuminating means includes:

a first illuminating means including paired first light projectors that project light toward the objective line in illuminating directions from the opposite sides, respectively, with respect to the objective line; and a second illuminating means including paired second light projectors that project light respectively from opposite sides toward the objective line in illuminating directions different from the illuminating directions in which the first illuminating means illuminates the objective line, respectively;

the tire surface inspection system further comprises:

a turning means for turning the support means to turn the tire; and a control means for controlling the line camera and the turning means;

wherein the control means carries out control operations for driving the turning means for turning such that the objective line is moved successively to different parts of the surface of the tire and for driving the line camera in synchronism with the illuminating operations of the first and second illuminating means such that images of parts of the surface of the tire successively brought into coincidence with the objective line are formed sequentially, wherein the paired first light projectors include first linear light projectors extending in a direction parallel to the objective line set on the surface of the tire, wherein the paired second light projectors include second linear projectors extending in a direction perpendicular to the objective line, and wherein the paired first light projectors and the paired second light projectors are arranged on four sides, respectively, of a quadrilateral having a diagonal parallel to the objective line as viewed in a direction toward the surface of the tire.

\* \* \* \* \*